United States Patent [19]

Maylotte

[11] Patent Number: 4,729,079
[45] Date of Patent: Mar. 1, 1988

[54] ILLUMINATOR FOR VISUAL INSPECTION OF CURVED SPECULAR SURFACES

[75] Inventor: Donald H. Maylotte, Schenectady, N.Y.

[73] Assignee: General Electric Company, Schenectady, N.Y.

[21] Appl. No.: 892,652

[22] Filed: Aug. 4, 1986

[51] Int. Cl.$^4$ .............................. F21V 7/00
[52] U.S. Cl. ....................... 362/350; 362/32; 362/247
[58] Field of Search ............... 362/32, 236, 247, 347, 362/350

[56] References Cited

U.S. PATENT DOCUMENTS

| | | | |
|---|---|---|---|
| 261,037 | 7/1882 | Plympton | 362/350 |
| 1,413,315 | 4/1922 | Correll | 362/350 |
| 1,648,955 | 11/1927 | McGinnis | 362/247 |
| 2,447,923 | 8/1948 | Tuck | 362/247 |
| 2,507,909 | 5/1950 | Kayser | 362/32 X |
| 3,786,243 | 1/1974 | Ilzig et al. | 362/32 |
| 4,242,727 | 12/1980 | de Vos | 362/347 X |
| 4,459,647 | 7/1984 | Yamauchi et al. | 362/347 X |
| 4,651,262 | 3/1987 | Piironen | 362/350 |

FOREIGN PATENT DOCUMENTS

| | | | |
|---|---|---|---|
| 2732805 | 2/1979 | Fed. Rep. of Germany | 362/32 |
| 2932622 | 2/1981 | Fed. Rep. of Germany | 362/350 |
| 1061834 | 4/1954 | France | 362/350 |
| 1085997 | 2/1955 | France | 362/350 |
| 269083 | 7/1970 | U.S.S.R. | 362/32 |

Primary Examiner—Stephen F. Husar
Attorney, Agent, or Firm—William H. Steinberg; James C. Davis, Jr.; Paul R. Webb, II

[57] ABSTRACT

An illuminator for providing high contrast illumination of curved surfaces is provided comprising a diffuse spherical reflector having an aperture at its peak. A source of radiant energy distributed along a ring, illuminates the interior of the reflector, which in turn illuminates the curved surfaces situated at the center of a sphere of which the spherical reflector is a part. Light reflected from the curved surfaces is reflected through the aperture.

1 Claim, 2 Drawing Figures

ILLUMINATOR FOR VISUAL INSPECTION OF CURVED SPECULAR SURFACES

The present invention relates to an illuminator for use in visual inspection of curved specular surfaces suitable for use with automated machine vision systems.

Machine vision applications rely on controlled lighting to provide the desired contrast needed to define the boundaries of parts to be inspected. In the inspection of solder pads on ceramic chips a number of lighting systems were tried to allow binary image processing. The solder pads after solder dipping appear as irregularly domed bumps 1-3 mils high on a rectangular base 4-6 mils on the sides. The surface of the solder bump is essentially a specular reflector. Circular fluorescent light sources were tried but were not sufficiently bright. A narrow ring of light provided by fiber optic strands arranged in a ring, resulted in a bright ring of light around a portion of the solder bump but did not illuminate the entire bump.

It is an object of the present invention to provide an illuminator that provides high contrast illumination of curved specular surfaces.

It is a further object of the present invention to provide an illuminator that provides high contrast illumination of curved specular surfaces sufficient to generate images that can be rapidly machine processed to give position information.

SUMMARY OF THE INVENTION

In one aspect of the present invention an illuminator for use in visual inspection systems for supplying high contrast lighting of curved surfaces is provided. The illuminator comprises a spherical reflector with a light diffusing coating on the interior wall. The reflector defines an aperture situated along an axis perpendicular to the plane passing through the largest circle of the spherical reflector, with the axis passing through the center of the largest circle. Means for uniformly illuminating the interior walls of the reflector are provided so that the curved surfaces to be illuminated, which can be positioned approximately in the center of a sphere of which the reflector is a part, can be illuminated by reflected light from the reflector walls which is then reflected from the curved surfaces to be inspected through the aperture.

BRIEF DESCRIPTION OF THE DRAWING

While the specification concludes with claims particularly pointing out and distinctly claiming the present invention, objects and advantages of the invention can be more readily ascertained from the following description of a preferred embodiment when used in conjunction with the accompanying drawing in which:

DETAILED DESCRIPTION OF THE INVENTION

Figure 1:
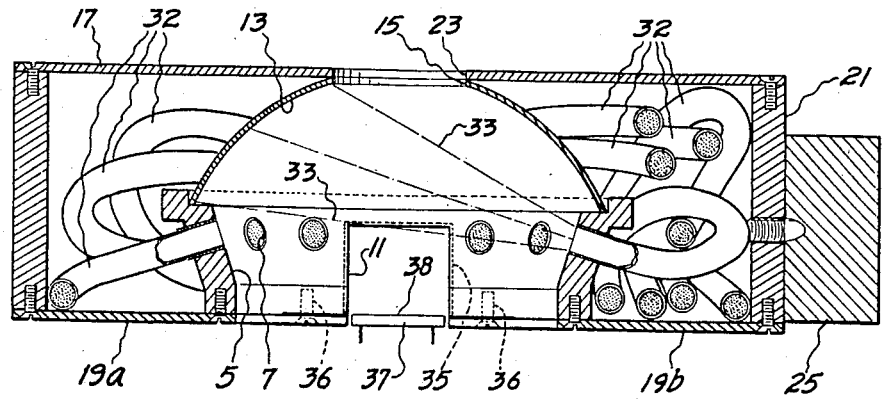
FIG. 1 is a sectional side view of the illuminator in accordance with the present invention, taken along the lines 1—1 of FIG. 2.
Figure 2:
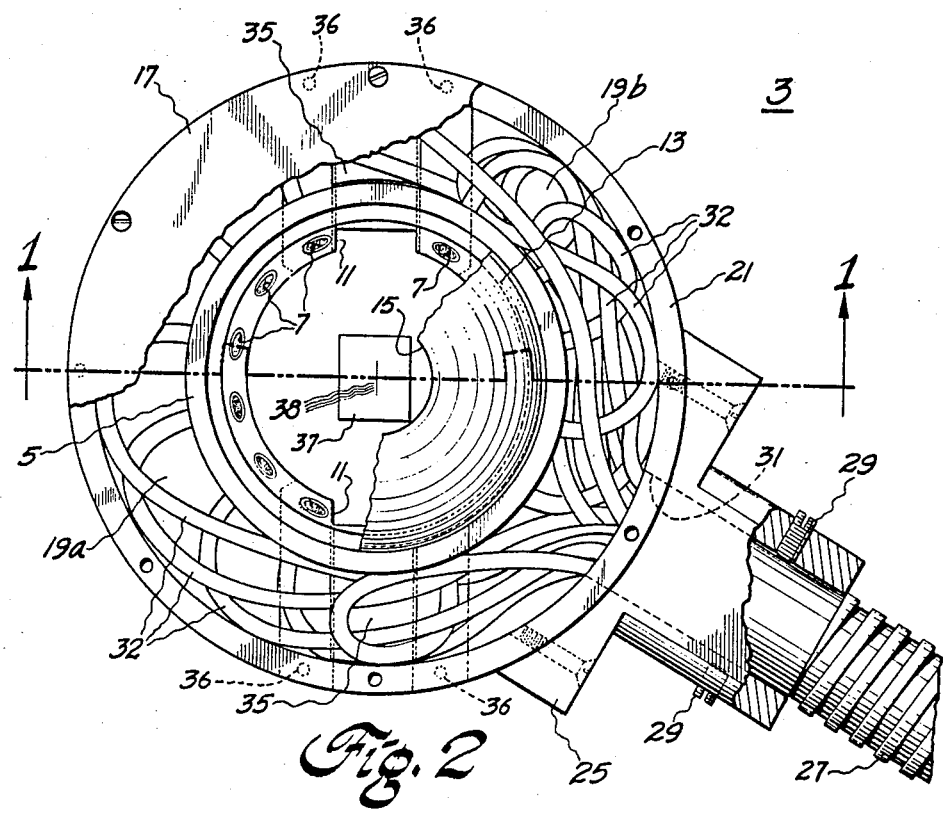
FIG. 2 is a partially cut-away plan view of the illuminator of FIG. 1.

Referring now to FIGS. 1 and 2, an illuminator 3 is shown for providing high contrast lighting of curved surfaces. The illuminator comprises a ring 5 fabricated from aluminum, for example, defining a plurality of radial circumferentially spaced apertures 7. The ring 5 has two rectangular notches 11 extending up from the bottom of the ring located on opposite sides of the ring. A spherical reflector 13 which comprises a spherical shell, which in the present embodiment is a portion of a hemisphere, is soldered at its periphery to a countersunk circular channel in the top of the ring. The spherical shell can be formed from a copper sheet. The spherical reflector has an aperture 15 at its peak.

The inside of the spherical reflector and ring is treated to obtain a diffuse light reflective finish such as by painting with flat white paint, and then covering the dried flat white paint with a paste of barium sulfate, water and methanol. The white paint provides a diffuse reflector in places where the paste does not adhere.

The ring 5 and spherical reflector 13 are situated in a cylindrical enclosure having a top plate 17, a two piece base plate 19a and b, and a cylindrical wall 21. The top plate 17 has an aperture 23 which aligns with the aperture 15 of reflector 13. The top plate 17 and reflector 13 are soldered to one another around the periphery of their respective apertures 23 and 15. The top plate is secured around its periphery to the cylindrical wall 21, such as by machine screws engaged in threaded holes in the cylindrical walls. The cylinder walls 21 have two rectangular notches extending up from the bottom of the wall. The notches are aligned with the notches 11 in the ring. A clamp 25 is secured to the outside of the cylindrical wall such as by screws engaged in threaded holes in the cylindrical wall. The clamp holds the flexible metal sheathing of a twelve bundle fiber optic light guide 27 with set screws 29. The clamp is aligned with an aperture 31 in the cylinder wall 21, through which the fiber optic bundles 32 pass.

The bottom plates 19a and 19b do not cover the opening in the center of the ring 5 or the notches 11 in the ring. In addition, the bottom plates leave a passageway the width of the notch from the ring to the notch in the cylindrical wall 21.

The twelve bundles 32 of fiber optic strands, each end in a metal can which secures the strands into a grouping with a circular cross section. The cans are forced fit into the aperture 7 so that the ends of the bundles are flush with the inside diameter of the ring. The radial apertures 7 are at an angle so that light emanating from each bundle points up from the horizontal plane illuminating a portion of the reflector wall above the opposite side of the ring from the bundle of strands providing the light. The section of the reflector illuminated, extends from the aperture 15 to the portion of the reflector mounted in the ring 5 as shown by dashed lines 33 in FIG. 1. In routing the fiber optic bundles from their introduction at the aperture 31 adjacent the clamp 25 to the apertures 7 in the ring, care is taken to avoid small radius turns which can cause breaking of the brittle fiber optic strands. The bundles of fiber optic strands are routed through the annular chamber defined by the outside of the ring 5 and reflector 13 and the inside of the cylindrical enclosure 21. Sheet material, such as copper sheet 35, is secured to base plates 19a and b by screws 36 and captured between the ring and base plates. The sheet material is bent to the shape of the notches in the ring and situated between the adjacent notches in the ring and cylindrical wall creating a passageway from each notch in the cylindrical wall to each notch in the ring, enclosed at the top and sides by the sheet. The copper sheet keeps the fiber optic bundles 32 out of the passageways which lead to the ring. Access to the center of the sphere, of which the spherical reflector is a portion, can be obtained by passing through the notch in the cylindrical wall, through the passageway to the notch in the ring and then inside the ring. A ceramic chip carrier 37 with a plurality of solder bumps 38 is shown situated in the center of the sphere, which the spherical reflector is a part.

In operation, the curved surfaces 38 to be illuminated, which are the specular solder bumps 38 on the surface of a chip carrier 37 in the present embodiment, can be placed generally in the center of the sphere of which the reflector is a part. The fiber optic light guide 27 is connected to a light source (not shown) illuminating the ring of fiber optic bundles. The fiber optic bundles illuminate the interior of the diffuse spherical reflector 13. The light striking the reflector 13 is reflected in all directions from all portions of the spherical reflector, illuminating the curved surface 38 of the chip carrier. The solder bumps are entirely illuminated by reflected light and in turn reflect light through the reflector aperture 15, where the light can be processed to obtain information regarding the curved surfaces. The light reflected through the aperture provides high contrast circular images with a small dark spot in the center. The dark spot in the center results from the position of the aperture 15 in the reflector which prevents vertical reflected light from reaching the peak of the solder bump.

The foregoing describes an illuminator that provides high contract illumination of curved specular surfaces sufficient to generate images that can be rapidly machine processed to give position information.

While the invention has been particular shown and described with reference to a preferred embodiment thereof, it will be understood by those skilled in the art that various changes in form and details may be made without departing from the spirit and scope of the invention.

What is claimed is:

1. An illuminator for use in visual inspection systems for providing high contrast lighting of an object having curved surfaces to be inspected, said illuminator comprising:

a spherical reflector with a light diffusing coating on the interior walls, said reflector defining an aperture situated along an axis perpendicular to the plane passing through the largest circle of the spherical reflector, the axis passing through the center of the largest circle; and means for uniformly illuminating the interior walls of the reflector, so that the object having curved surfaces to be inspected, positioned approximately in the center of a sphere of which the reflector is a part, can be illuminated by reflected light from the reflector wall, which then can be reflected from the curved surface to be inspected through the aperture.

* * * * *